United States Patent
Arora et al.

(10) Patent No.: US 11,578,370 B2
(45) Date of Patent: Feb. 14, 2023

(54) METHODS FOR DIAGNOSIS AND TREATMENT OF PATIENTS HAVING SOLID TUMORS

(71) Applicant: Institute For Cancer Research, Philadelphia, PA (US)

(72) Inventors: Sanjeevani Arora, Philadelphia, PA (US); Joshua Meyer, Philadelphia, PA (US); Erica Golemis, Philadelphia, PA (US); Randy Lesh, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 799 days.

(21) Appl. No.: 16/485,977

(22) PCT Filed: Feb. 14, 2018

(86) PCT No.: PCT/US2018/018110
§ 371 (c)(1),
(2) Date: Aug. 14, 2019

(87) PCT Pub. No.: WO2018/152154
PCT Pub. Date: Aug. 23, 2018

(65) Prior Publication Data
US 2020/0232041 A1   Jul. 23, 2020

Related U.S. Application Data

(60) Provisional application No. 62/459,229, filed on Feb. 15, 2017.

(51) Int. Cl.
| G01N 31/00 | (2006.01) |
| G01N 33/53 | (2006.01) |
| C12Q 1/6886 | (2018.01) |
| G01N 33/574 | (2006.01) |
| C12Q 1/68 | (2018.01) |
| G01N 33/68 | (2006.01) |

(52) U.S. Cl.
CPC ............. *C12Q 1/6886* (2013.01); *C12Q 1/68* (2013.01); *G01N 33/57407* (2013.01); *G01N 33/57423* (2013.01); *G01N 33/57434* (2013.01); *G01N 33/57488* (2013.01); *G01N 33/6875* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

2012/0288861 A1   11/2012   Lenz
2016/0041175 A1 * 2/2016   Ezrin ................. G01N 33/6875
435/7.92

OTHER PUBLICATIONS

Celeste et al. (Cell, 2003, vol. 114, No. 3, pp. 371-383) (Year: 2003).*
Taneja et al. (Journal of Biol. Chem. 2004, vol. 279, No. 3, pp. 2273-2280). (Year: 2004).*
Celeste et al., "H2AX Haploinsufficiency Modifies Genomic Stability and Tumor Susceptibility", Cell, 2003,114 (3):371-383.
Taneja et al., "Histone H2AX Phosphorylation as a Predictor of Radiosensitivity and Targer For Radiotherapy", J. Biol. Chem., 2004, 279(3):2273-2280.

* cited by examiner

*Primary Examiner* — Lisa V Cook
(74) *Attorney, Agent, or Firm* — Armstrong Teasdale LLP

(57) ABSTRACT

Methods for diagnosing a subject as a candidate for removal of a solid tumor without preoperative chemoradiation therapy, and methods for treating patients having solid tumors, who have one or more of genomic instability, elevated double stranded DNA breaks, elevated gamma-H2AX foci, or elevated replication stress and/or double stranded break-signalling (DSB-signalling) biomarkers in peripheral blood lymphocytes (PBLs) are provided herein.

11 Claims, 2 Drawing Sheets

METHODS FOR DIAGNOSIS AND TREATMENT OF PATIENTS HAVING SOLID TUMORS

FIELD

The disclosure relates generally to the field of cancer diagnosis and treatment. More particularly, the disclosure relates to methods for diagnosing a subject as a candidate for removal of a solid tumor without preoperative chemoradiation therapy, and to methods for treating patients having solid tumors, who have one or more of genomic instability, elevated double stranded DNA breaks, elevated gamma-H2AX foci, or elevated replication stress and/or double stranded break-signalling (DSB-signalling) biomarkers in peripheral blood lymphocytes (PBLs).

BACKGROUND

Rectal cancer is a common disease, with an estimated incidence of approximately 39,220 patients in the United States (American Cancer Society: Cancer Facts and Figures 2016. Atlanta, Ga.: American Cancer Society, 2016). Neo-adjuvant chemoradiation therapy (nCRT) or pre-operative chemoradiation therapy is considered the preferable adjuvant standard of care in the management of locally advanced (stage II/III) rectal cancer (Preoperative short-term radiation therapy in operable rectal carcinoma. A prospective randomized trial. Stockholm Rectal Cancer Study Group. Cancer 1990, 66, 49-55). However, not all patients respond to chemoradiation therapy (CRT) and it is hard to segregate likely responders and non-responders to CRT.

Radiation treatment is not without side effects, both acute and chronic; so optimal patient selection is important in limiting the number of patients who are harmed by radiation without benefit. One recent study found 14% of patients suffered from grade 3 or 4 toxicity (Tepper et al., J. Clin. Oncol., 2011, 29, 4604-4606). Neoadjuvant chemoradiation produces a pathologic complete response (pCR) in approximately 20%-30% of patients, affording these patients improved overall survival. The absence of residual cancer in resected specimens following neoadjuvant chemoradiation (ypT0) have led some authors to question the need for radical surgical resection of the rectum, and propose observation or local excision to confirm pathologic CR and remove persistent disease (Habr-Gama, Colorectal Dis., 2006, 8, Suppl. 3, 21-24). Conversely, approximately one third of patients show minimal to no pathologic response following chemoradiation, and therefore may not benefit from the treatment (Roy et al., J. Surg. Oncol., 2012, 105, 130-134).

nCRT is currently also the standard treatment for locally advanced esophageal carcinoma (EC) and advanced lung cancers. Locally advanced EC accounts for about 57% of newly diagnosed patients. For many patients, nCRT has been demonstrated to deliver substantial benefit; however, complete eradication of the tumor occurs in only about 30% of patients who receive nCRT, and CRT is toxic. At present, there is no clinically actionable biomarker to predict which EC patients are likely to respond to nCRT. As a result, many patients are exposed to this toxic, DNA damaging therapy (radiation and chemotherapy) without benefit. Therefore, it is important to be able to identify patients a priori who have a higher likelihood of responding to nCRT. Thus, it is extremely valuable to develop biomarkers that may help predict response to pre-operative CRT.

SUMMARY

The present disclosure provides methods for diagnosing a subject as a candidate for removal of a solid tumor without preoperative chemoradiation therapy, and to methods of treating a solid tumor in a subject in need thereof. The subject is preferably a human.

The present disclosure also provides methods for diagnosing a subject as a candidate for removal of a solid tumor without preoperative chemoradiation therapy comprising: detecting the presence or absence of any one or more of i) genomic instability, ii) double stranded DNA breaks, iii) gamma-H2AX foci, and iv) a replication stress and/or DSB-signalling biomarker, in isolated peripheral blood lymphocytes from the subject having the solid tumor; wherein the absence of an elevated level of all of i), ii), iii), and iv) compared to a subject not having a solid tumor indicates that the subject is a candidate for removal of the solid tumor without preoperative chemoradiation therapy; and wherein the presence of an elevated level of any one or more of i), ii), iii), and iv) compared to a subject not having a solid tumor indicates that the subject is a candidate for removal of the solid tumor after receiving preoperative chemoradiation therapy.

The present disclosure also provides methods for treating a subject having a solid tumor comprising: detecting the presence or absence of any one or more of i) genomic instability, ii) double stranded DNA breaks, iii) gamma-H2AX foci, and iv) a replication stress and/or DSB-signalling biomarker, in isolated peripheral blood lymphocytes from the subject having the solid tumor; and i) removing the solid tumor from the subject without preoperative chemoradiation therapy when the absence of an elevated level of all of i), ii), iii), and iv) compared to a subject not having a solid tumor exists; or ii) treating the subject with preoperative chemoradiation therapy prior to removing the solid tumor from the subject when the presence of an elevated level of any one or more of i), ii), iii), and iv) compared to a subject not having a solid tumor exists.

In some embodiments, the methods for treating a solid tumor in a subject comprise detecting genomic instability, double stranded DNA breaks, levels of gamma-H2AX foci, and/or elevated levels of replication stress and/or DSB-signalling biomarkers in isolated PBLs from the subject having the solid tumor that are elevated over desired levels, and treating the subject with preoperative chemoradiation therapy prior to optional surgery to remove the solid tumor. In some embodiments, where genomic instability, double stranded DNA breaks, levels of gamma-H2AX foci and/or elevated levels of replication stress and/or DSB-signalling biomarkers are not detected, the solid tumor is removed from the subject by surgery without the subject undergoing preoperative chemoradiation therapy. Prior to the detecting step, the nucleus, nuclear material, or nucleic acids may be isolated from the peripheral blood lymphocytes, such that the detection of genomic instability, double stranded DNA breaks, elevated levels of gamma-H2AX foci and/or elevated levels of replication stress and/or DSB-signalling biomarkers may be carried out on a nucleus, nuclear material, or nucleic acids. In some embodiments, the method further comprises contacting the peripheral blood lymphocytes with a low dose of a DNA damaging agent, such as aphidicolin, or ionizing radiation, and this contacting step may be carried out prior to isolating the nucleus, nuclear material, or nucleic acids from the lymphocytes where such isolating is employed. In some embodiments, the solid tumor is rectal cancer, esophageal cancer or lung cancer. In some embodiments, the rectal cancer is Stage II rectal cancer. In some embodiments, the rectal cancer is Stage III rectal cancer. In some embodiments, the replication stress biomarker is replication protein A (RPA), ataxia telangiectasia and Rad3-related (ATR), or checkpoint kinase 1 (CHK1), and the DSB-signalling biomarker is phospho-ataxia telangiectasia mutated (phospho-ATM) or checkpoint kinase 2 (CHK2). In some embodiments, the replication stress biomarker is replication protein A (RPA) and the DSB-signalling biomarker is phospho-ataxia telangiectasia mutated (phospho-ATM).

In some embodiments, the methods for treating a solid tumor in a subject comprise detecting double stranded DNA breaks in isolated PBLs from the subject having the solid tumor that are elevated over desired levels, and treating the subject with preoperative chemoradiation therapy prior to optional surgery to remove the tumor. In some embodiments, where double stranded DNA breaks are not detected, in the peripheral blood lymphocytes, the tumor is removed from the subject by surgery without the subject undergoing preoperative chemoradiation therapy. Prior to the detecting step, the nucleus, nuclear material, or nucleic acids may be isolated from the peripheral blood lymphocytes, such that the detection of double stranded DNA breaks may be carried out on a nucleus, nuclear material, or nucleic acids. In some embodiments, the method further comprises contacting the peripheral blood lymphocytes with a low dose of a DNA damaging agent, or with a low dose of aphidicolin or ionizing radiation, and this contacting step may be carried out prior to isolating the nucleus, nuclear material, or nucleic acids from the lymphocytes where such isolating is employed. In some embodiments, the solid tumor is rectal cancer, esophageal cancer or lung cancer. In some embodiments, the rectal cancer is Stage II rectal cancer. In some embodiments, the rectal cancer is Stage III rectal cancer.

In some embodiments, the methods for treating a solid tumor in a subject comprise detecting genomic instability in isolated PBLs from the subject having the solid tumor that are elevated over desired levels, and treating the subject with preoperative chemoradiation therapy prior to optional surgery to remove the tumor. In some embodiments, where genomic instability is not detected, in the peripheral blood lymphocytes, the tumor is removed from the subject by surgery without the subject undergoing preoperative chemoradiation therapy. Prior to the detecting step, the nucleus, nuclear material, or nucleic acids may be isolated from the peripheral blood lymphocytes, such that the detection of genomic instability may be carried out on a nucleus, nuclear material, or nucleic acids. In some embodiments, the method further comprises contacting the peripheral blood lymphocytes with a low dose of a DNA damaging agent, such as aphidicolin, or ionizing radiation, and this contacting step may be carried out prior to isolating the nucleus, nuclear material, or nucleic acids from the lymphocytes where such isolating is employed. In some embodiments, the solid tumor is rectal cancer, esophageal cancer or lung cancer. In some embodiments, the rectal cancer is Stage II rectal cancer. In some embodiments, the rectal cancer is Stage III rectal cancer.

In some embodiments, the methods for treating a solid tumor in a subject comprise detecting levels of gamma-H2AX foci in isolated PBLs from the subject having the solid tumor that are elevated over desired levels, and treating the subject with preoperative chemoradiation therapy prior to optional surgery to remove the tumor. In some embodiments, where levels of gamma-H2AX foci elevated over desired levels of gamma-H2AX foci are not detected, in the peripheral blood lymphocytes, the tumor is removed from the subject by surgery without the subject undergoing preoperative chemoradiation therapy. Prior to the detecting step, the nucleus, nuclear material, or nucleic acids may be isolated from the peripheral blood lymphocytes, such that the detection of elevated levels of gamma-H2AX foci may be carried out on a nucleus, nuclear material, or nucleic acids. In some embodiments, the method further comprises contacting the peripheral blood lymphocytes with a low dose of a DNA damaging agent, such as aphidicolin, or ionizing radiation, and this contacting step may be carried out prior to isolating the nucleus, nuclear material, or nucleic acids from the lymphocytes where such isolating is employed. In some embodiments, the solid tumor is rectal cancer, esophageal cancer or lung cancer. In some embodiments, the rectal cancer is Stage II rectal cancer. In some embodiments, the rectal cancer is Stage III rectal cancer.

In some embodiments, the methods for treating a solid tumor in a subject comprise detecting elevated levels of replication stress and/or DSB-signalling biomarkers in isolated PBLs from the subject having the solid tumor that are elevated over desired levels, and treating the subject with preoperative chemoradiation therapy prior to optional surgery to remove the solid tumor. In some embodiments, where elevated levels of replication stress and/or DSB-signalling biomarkers are not detected, the solid tumor is removed from the subject by surgery without the subject undergoing preoperative chemoradiation therapy. Prior to the detecting step, the nucleus, nuclear material, or nucleic acids may be isolated from the peripheral blood lymphocytes, such that the detection of elevated levels of replication stress and/or DSB-signalling biomarkers may be carried out on a nucleus, nuclear material, or nucleic acids. In some embodiments, the method further comprises contacting the peripheral blood lymphocytes with a low dose of a DNA damaging agent, such as aphidicolin, or ionizing radiation, and this contacting step may be carried out prior to isolating the nucleus, nuclear material, or nucleic acids from the lymphocytes where such isolating is employed. In some embodiments, the solid tumor is rectal cancer, esophageal cancer or lung cancer. In some embodiments, the rectal cancer is Stage II rectal cancer. In some embodiments, the rectal cancer is Stage III rectal cancer. In some embodiments, the replication stress biomarker is replication protein A (RPA), ataxia telangiectasia and Rad3-related (ATR), or checkpoint kinase 1 (CHK1), and the DSB-signalling biomarker is phospho-ataxia telangiectasia mutated (phospho-ATM) or checkpoint kinase 2 (CHK2). In some embodiments, the replication stress biomarker is replication protein A (RPA) and the DSB-signalling biomarker is phospho-ataxia telangiectasia mutated (phospho-ATM).

In some embodiments, the methods for treating a solid tumor in a subject comprise detecting genomic instability and double stranded DNA breaks in isolated PBLs from the subject having the solid tumor that are elevated over desired levels, and treating the subject with preoperative chemoradiation therapy prior to optional surgery to remove the tumor. In some embodiments, where genomic instability and double stranded DNA breaks are not detected, in the peripheral blood lymphocytes, the tumor is removed from the subject by surgery without the subject undergoing preoperative chemoradiation therapy. Prior to the detecting step, the nucleus, nuclear material, or nucleic acids may be isolated from the peripheral blood lymphocytes, such that the detection of genomic instability and double stranded DNA breaks may be carried out on a nucleus, nuclear material, or nucleic acids. In some embodiments, the method further comprises contacting the peripheral blood lymphocytes with a low dose of a DNA damaging agent, such as aphidicolin, or ionizing radiation, and this contacting step may be carried out prior to isolating the nucleus, nuclear material, or nucleic acids from the lymphocytes where such isolating is employed. In some embodiments, the solid tumor is rectal cancer, esophageal cancer or lung cancer. In some embodiments, the rectal cancer is Stage II rectal cancer. In some embodiments, the rectal cancer is Stage III rectal cancer.

In some embodiments, the methods for treating a solid tumor in a subject comprise detecting genomic instability and levels of gamma-H2AX foci in isolated PBLs from the subject having the solid tumor that are elevated over desired levels, and treating the subject with preoperative chemoradiation therapy prior to optional surgery to remove the tumor. In some embodiments, where genomic instability and levels of gamma-H2AX foci elevated over desired levels of gamma-H2AX foci are not detected, in the peripheral blood lymphocytes, the tumor is removed from the subject by surgery without the subject undergoing preoperative chemoradiation therapy. Prior to the detecting step, the nucleus, nuclear material, or nucleic acids may be isolated from the peripheral blood lymphocytes, such that the detection of genomic instability and elevated levels of gamma-H2AX foci may be carried out on a nucleus, nuclear material, or nucleic acids. In some embodiments, the method further comprises contacting the peripheral blood lymphocytes with a low dose of a DNA damaging agent, such as aphidicolin, or ionizing radiation, and this contacting step may be carried out prior to isolating the nucleus, nuclear material, or nucleic acids from the lymphocytes where such isolating is employed. In some embodiments, the solid tumor is rectal cancer, esophageal cancer or lung cancer. In some embodiments, the rectal cancer is Stage II rectal cancer. In some embodiments, the rectal cancer is Stage III rectal cancer.

In some embodiments, the methods for treating a solid tumor in a subject comprise detecting double stranded DNA breaks and levels of gamma-H2AX foci in isolated PBLs from the subject having the solid tumor that are elevated over desired levels, and treating the subject with preoperative chemoradiation therapy prior to optional surgery to remove the tumor. In some embodiments, where double stranded DNA breaks and levels of gamma-H2AX foci elevated over desired levels of gamma-H2AX foci are not detected, in the peripheral blood lymphocytes, the tumor is removed from the subject by surgery without the subject undergoing preoperative chemoradiation therapy. Prior to the detecting step, the nucleus, nuclear material, or nucleic acids may be isolated from the peripheral blood lymphocytes, such that the detection of double stranded DNA breaks and elevated levels of gamma-H2AX foci may be carried out on a nucleus, nuclear material, or nucleic acids. In some embodiments, the method further comprises contacting the peripheral blood lymphocytes with a low dose of a DNA damaging agent, such as aphidicolin, or ionizing radiation, and this contacting step may be carried out prior to isolating the nucleus, nuclear material, or nucleic acids from the lymphocytes where such isolating is employed. In some embodiments, the solid tumor is rectal cancer, esophageal cancer or lung cancer. In some embodiments, the rectal cancer is Stage II rectal cancer. In some embodiments, the rectal cancer is Stage III rectal cancer.

In some embodiments, the methods for treating a solid tumor in a subject comprise detecting genomic instability and elevated levels of replication stress and/or DSB-signalling biomarkers in isolated PBLs from the subject having the solid tumor that are elevated over desired levels, and treating the subject with preoperative chemoradiation therapy prior to optional surgery to remove the solid tumor. In some embodiments, where genomic instability and elevated levels of replication stress and/or DSB-signalling biomarkers are not detected, the solid tumor is removed from the subject by surgery without the subject undergoing preoperative chemoradiation therapy. Prior to the detecting step, the nucleus, nuclear material, or nucleic acids may be isolated from the peripheral blood lymphocytes, such that the detection of genomic instability and elevated levels of replication stress and/or DSB-signalling biomarkers may be carried out on a nucleus, nuclear material, or nucleic acids. In some embodiments, the method further comprises contacting the peripheral blood lymphocytes with a low dose of a DNA damaging agent, such as aphidicolin, or ionizing radiation, and this contacting step may be carried out prior to isolating the nucleus, nuclear material, or nucleic acids from the lymphocytes where such isolating is employed. In some embodiments, the solid tumor is rectal cancer, esophageal cancer or lung cancer. In some embodiments, the rectal cancer is Stage II rectal cancer. In some embodiments, the rectal cancer is Stage III rectal cancer. In some embodiments, the replication stress biomarker is replication protein A (RPA), ataxia telangiectasia and Rad3-related (ATR), or checkpoint kinase 1 (CHK1), and the DSB-signalling biomarker is phospho-ataxia telangiectasia mutated (phospho-ATM) or checkpoint kinase 2 (CHK2). In some embodiments, the replication stress biomarker is replication protein A (RPA) and the DSB-signalling biomarker is phospho-ataxia telangiectasia mutated (phospho-ATM).

In some embodiments, the methods for treating a solid tumor in a subject comprise detecting double stranded DNA breaks and elevated levels of replication stress and/or DSB-signalling biomarkers in isolated PBLs from the subject having the solid tumor that are elevated over desired levels, and treating the subject with preoperative chemoradiation therapy prior to optional surgery to remove the solid tumor. In some embodiments, where double stranded DNA breaks and elevated levels of replication stress and/or DSB-signalling biomarkers are not detected, the solid tumor is removed from the subject by surgery without the subject undergoing preoperative chemoradiation therapy. Prior to the detecting step, the nucleus, nuclear material, or nucleic acids may be isolated from the peripheral blood lymphocytes, such that the detection of double stranded DNA breaks and elevated levels of replication stress and/or DSB-signalling biomarkers may be carried out on a nucleus, nuclear material, or nucleic acids. In some embodiments, the method further comprises contacting the peripheral blood lymphocytes with a low dose of a DNA damaging agent, such as aphidicolin, or ionizing radiation, and this contacting step may be carried out prior to isolating the nucleus, nuclear material, or nucleic acids from the lymphocytes where such isolating is employed. In some embodiments, the solid tumor is rectal cancer, esophageal cancer or lung cancer. In some embodiments, the rectal cancer is Stage II rectal cancer. In some embodiments, the rectal cancer is Stage III rectal cancer. In some embodiments, the replication stress biomarker is replication protein A (RPA), ataxia telangiectasia and Rad3-related (ATR), or checkpoint kinase 1 (CHK1), and the DSB-signalling biomarker is phospho-ataxia telangiectasia mutated (phospho-ATM) or checkpoint kinase 2 (CHK2). In some embodiments, the replication stress biomarker is replication protein A (RPA) and the DSB-signalling biomarker is phospho-ataxia telangiectasia mutated (phospho-ATM).

In some embodiments, the methods for treating a solid tumor in a subject comprise detecting elevated levels of gamma-H2AX foci and elevated levels of replication stress and/or DSB-signalling biomarkers in isolated PBLs from the subject having the solid tumor that are elevated over desired levels, and treating the subject with preoperative chemoradiation therapy prior to optional surgery to remove the solid tumor. In some embodiments, where elevated levels of gamma-H2AX foci and elevated levels of replication stress and/or DSB-signalling biomarkers are not detected, the solid tumor is removed from the subject by surgery without the subject undergoing preoperative chemoradiation therapy. Prior to the detecting step, the nucleus, nuclear material, or nucleic acids may be isolated from the peripheral blood lymphocytes, such that the detection of elevated levels of gamma-H2AX foci and elevated levels of replication stress and/or DSB-signalling biomarkers may be carried out on a nucleus, nuclear material, or nucleic acids. In some embodiments, the method further comprises contacting the peripheral blood lymphocytes with a low dose of a DNA damaging agent, such as aphidicolin, or ionizing radiation, and this contacting step may be carried out prior to isolating the nucleus, nuclear material, or nucleic acids from the lymphocytes where such isolating is employed. In some embodiments, the solid tumor is rectal cancer, esophageal cancer or lung cancer. In some embodiments, the rectal cancer is Stage II rectal cancer. In some embodiments, the rectal cancer is Stage III rectal cancer. In some embodiments, the replication stress biomarker is replication protein A (RPA), ataxia telangiectasia and Rad3-related (ATR), or checkpoint kinase 1 (CHK1), and the DSB-signalling biomarker is phospho-ataxia telangiectasia mutated (phospho-ATM) or checkpoint kinase 2 (CHK2). In some embodiments, the replication stress biomarker is replication protein A (RPA) and the DSB-signalling biomarker is phospho-ataxia telangiectasia mutated (phospho-ATM).

DETAILED DESCRIPTION

Figure 1:
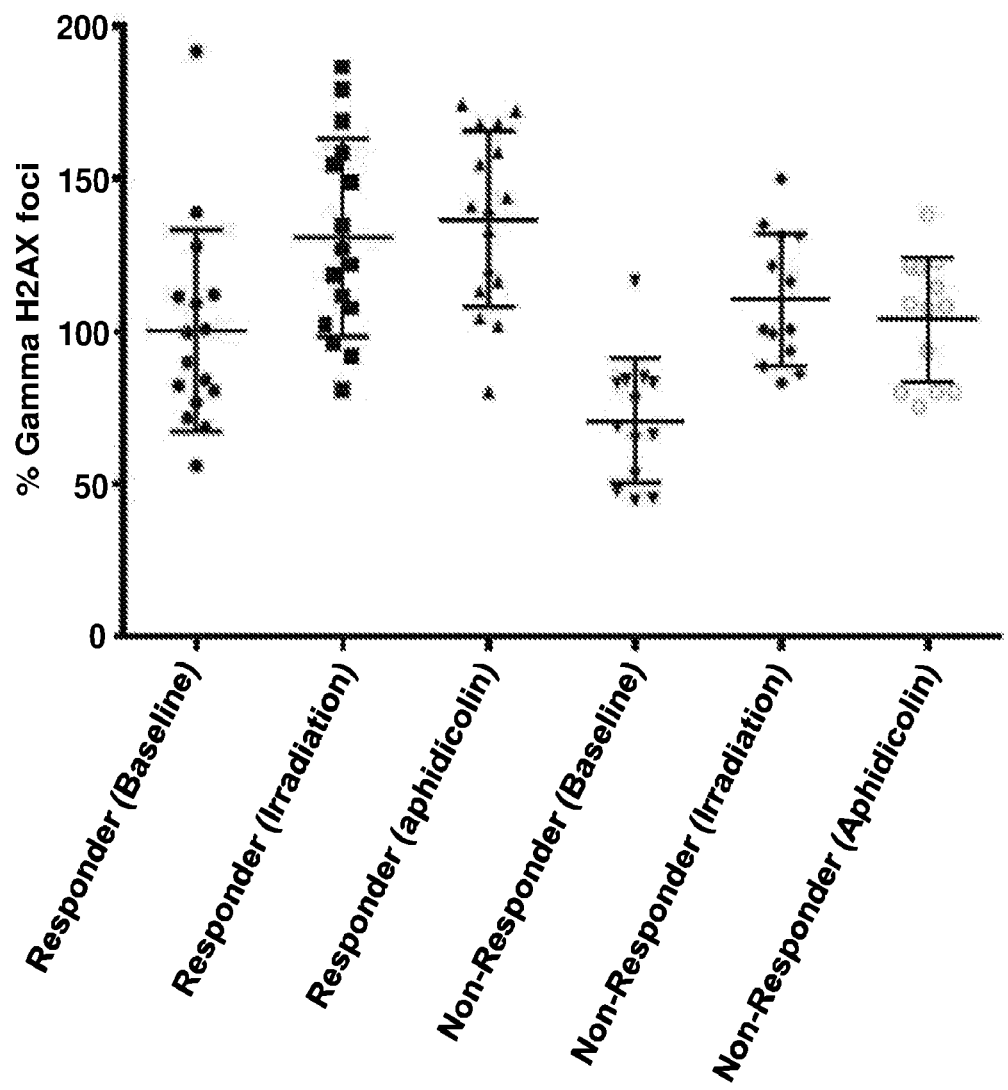
FIG. 1 shows elevated γH2AX in T-cells from chemoradiation therapy (CRT) responder cohort vs. non-responder cohort of rectal cancer patients at baseline and following treatment with DNA damaging agents.

Various terms relating to aspects of the present disclosure are used throughout the specification and claims. Such terms are to be given their ordinary meaning in the art, unless otherwise indicated. Other specifically defined terms are to be construed in a manner consistent with the definition provided in this document.

As used throughout, the singular forms "a," "an," and "the" include plural referents unless expressly stated otherwise.

A cell, a cell nucleus, cell nuclear material, or a molecule such as a polynucleotide or polypeptide has been "isolated" or "obtained" if it has been removed from its natural environment and/or altered by the hand of a human being.

The terms subject and patient are used interchangeably. A subject may be any animal, and preferably is a mammal. A mammalian subject may be a farm animal (e.g., sheep, horse, cow, pig), a companion animal (e.g., cat, dog), a rodent or laboratory animal (e.g., mouse, rat, rabbit), or a non-human primate (e.g., old world monkey, new world monkey). In some embodiments, the subject is a human.

The occurrence of solid tumors such as, for example, rectal and colorectal cancers have been linked to genetic changes such as defects in genes mediating DNA damage response and DNA repair. For example, microsatellite instability-high, also associated with Lynch syndrome-related rectal cancer, was shown to be associated with improved survival independent of tumor stage in a population-based series of 607 patients with colorectal cancer who were 50 years old or younger at the time of diagnosis. Additionally, gene expression profiling has been reported to be useful in predicting the response of rectal adenocarcinomas to preoperative CRT and in determining the prognosis of locally advanced (stages II and III) rectal cancer after neoadjuvant 5-fluorouracil-based CRT. The standard of care for the chemotherapy arm of chemoradiation therapy is either 5-Fluorouracil (5-FU) or capecitabine.

It has been observed in accordance with the present disclosure that the presence of one or more of genomic instability, double stranded DNA breaks, elevated levels of gamma H2AX foci, and elevated levels of replication stress and/or DSB-signalling biomarkers in peripheral blood lymphocytes are predictive as to whether a rectal cancer patient, particularly a patient with Stage II or Stage III rectal cancer, will respond positively to chemoradiation therapy (CRT). Stage II or Stage III rectal cancer patients found to have genomic instability, double stranded DNA breaks (DSB), elevated levels of gamma H2AX foci, and/or and elevated levels of replication stress and/or DSB-signalling biomarkers were observed to have maximal benefit from chemoradiation therapy prior to surgery. Therefore, such patients may benefit from receiving preoperative CRT prior to surgery. In contrast, Stage II or Stage III rectal cancer patients not found to have genomic instability, double stranded DNA breaks (DSB), elevated levels of gamma H2AX foci, and/or and elevated levels of replication stress and/or DSB-signalling biomarkers were observed to have minimal benefit from chemoradiation therapy prior to surgery. Therefore, such patients may benefit from avoidance of preoperative CRT or, in the alternative, may benefit from a change in the chemotherapeutic regimen that is part of the preoperative CRT. Such patients may therefore have surgery without preoperative CRT, and this represents a deviation from the standard of care in treatment of solid tumors, such as rectal cancer. Thus, genomic instability, double stranded DNA breaks, enhanced gamma-H2AX foci, and/or and elevated levels of replication stress and/or DSB-signalling biomarkers may serve as markers for a positive response to CRT. Accordingly, the present disclosure provides methods for diagnosis and treating of solid tumors, such as rectal cancer, by assessing patient peripheral blood lymphocytes for the presence of one or more of genomic instability, double stranded DNA breaks, elevated levels of gamma H2AX foci, and/or and elevated levels of replication stress and/or DSB-signalling biomarkers, and, where present, treating the patient with preoperative CRT prior to surgically removing the tumor.

In some embodiments, the methods further comprise isolating peripheral blood lymphocytes from a subject having a solid tumor. In some embodiments, the solid tumor is rectal cancer, esophageal cancer or lung cancer. In some embodiments, the rectal cancer is Stage II rectal cancer. In some embodiments, the rectal cancer is Stage III rectal cancer. Blood isolation may be according to any suitable methodology. The peripheral blood lymphocytes may be further isolated from the blood prior to screening. No significant differences in γ-H2AX between nCRT-naive and post-nCRT primary (or p) PBLs (p=0.519, n=11, by paired Wilcoxon test; PBL samples matched by pre- and post-treatment collection date). This was tested by high-throughput imaging of γ-H2AX (phosphorylated histone H2AX) a well-described marker of DNA double strand breaks (DSBs) in pPBLs of patients in the study. These results indicate that either treatment-naive or post-treatment primary PBLs can be used in situations where only a limited number of samples is available. A larger implication is that differences between complete and poor responders in response to nCRT are due to germline differences. Thus, the difference in response to nCRT may depend on variation in DNA-damage response and repair capacity in the subject's germline.

The screen or diagnostic for genomic instability, double stranded DNA breaks, enhanced gamma-H2AX foci, and/or and elevated levels of replication stress and/or DSB-signalling biomarkers can be carried out using nuclear material and nucleic acids obtained/isolated from peripheral blood lymphocytes. Thus, in some embodiments, the methods comprise isolating the nucleus, nuclear material and/or nucleic acids from the peripheral blood lymphocytes. The nucleic acid may be any nucleic acid that has, or from which may be determined, the presence and/or quantity of genomic instability, double stranded DNA breaks, and/or and elevated levels of replication stress and/or DSB-signalling biomarkers, and the cell or nucleus may be any cell or nucleus that has, or from which may be determined, the presence and/or quantity of gamma-H2AX foci.

In some embodiments where the screening or diagnostic method includes assessment of genomic instability, double stranded DNA breaks, enhanced gamma-H2AX foci, and/or and elevated levels of replication stress and/or DSB-signalling biomarkers, the genomic instability, double stranded DNA breaks, and/or and elevated levels of replication stress and/or DSB-signalling biomarkers may be detected from nucleic acids from the peripheral blood lymphocytes, and gamma-H2AX foci may be detected from the lymphocytes or nucleus thereof. Detecting genomic instability, double stranded DNA breaks, gamma-H2AX foci, and/or and elevated levels of replication stress and/or DSB-signalling biomarkers may be carried out according to any suitable method, including the methods described or exemplified herein. The detected genomic instability, double stranded DNA breaks, gamma-H2AX foci, and/or and elevated levels of replication stress and/or DSB-signalling biomarkers may be compared with quantitative or qualitative reference values for genomic instability, double stranded DNA breaks, gamma-H2AX foci, and/or and elevated levels of replication stress and/or DSB-signalling biomarkers associated with responsiveness or non-responsiveness to preoperative CRT. The reference values may, for example, comprise values indicative of a high probability of responding or not responding to preoperative CRT, values indicative of a moderate probability of responding or not responding to preoperative CRT, and/or values indicative of a low probability of responding or not responding to preoperative CRT. The comparing step may be carried out using a processor programmed to compare detected quantitative or qualitative values for genomic instability, double stranded DNA breaks, gamma-H2AX foci, and/or and elevated levels of replication stress and/or DSB-signalling biomarkers with quantitative or qualitative reference values for such markers. The comparison may be made between the subject sample being tested and a sample from a subject who is known not to have a solid tumor. Alternately, the comparison may be made between the subject sample being tested and one or more reference values (e.g., high, moderate, or low probability of responding or not responding to preoperative CRT), which may be derived from a subject population which is known not to have a solid tumor.

In some embodiments, the peripheral blood lymphocytes may be contacted with a DNA damaging agent, or with DNA damaging radiation prior to screening for genomic instability, double stranded DNA breaks, gamma-H2AX foci, and/or and elevated levels of replication stress and/or DSB-signalling biomarkers. The DNA damaging agent may induce double stranded breaks in DNA. The DNA damaging agent may include any agent that activates the double stranded DNA break repair system in a cell. The DNA damaging agent may comprise aphidicolin or ionizing radiation. The DNA damaging agent or radiation can be contacted with the lymphocytes at a low dose or sub-optimal dose. A low dose may include an amount of the agent or radiation that is lower than the manufacturer's recommended amount for a DNA damage assay. A low dose enhances the double stranded breaks and gamma-H2AX foci sufficient to give the screen higher confidence, but does not produce an excessive amount of background noise/DNA breaks.

Gamma-H2AX foci may be detected, for example, using immunoblotting, immunofluorescence, immunohistochemistry, ELISA, flow cytometry, or other methodology that includes, for example, a detectably-labeled antibody that specifically binds to gamma-H2AX foci. The foci may be assessed in permeabilized peripheral blood lymphocytes. Detection of the detectably-labeled antibody may thus visualize the foci, and may serve as the basis for quantification. Genomic instability may be detected, for example, from a metaphase spread or a karyotype obtained from the lymphocytes. A desired level of gamma-H2AX foci can be found, for example, in a human that does not have a rectal tumor. Thus, a human having levels of gamma-H2AX foci that are elevated over desired levels of gamma-H2AX foci may be suspected of having a rectal tumor.

Detection of one or more of genomic instability, double stranded DNA breaks, enhanced gamma-H2AX foci, and/or and elevated levels of replication stress and/or DSB-signalling biomarkers may serve as biomarkers indicating that the subject is likely to substantially positively respond to preoperative chemoradiation therapy. Once the one or more of genomic instability, double stranded DNA breaks, enhanced gamma-H2AX foci, and/or and elevated levels of replication stress and/or DSB-signalling biomarkers are detected, the standard of care for the rectal cancer patient is altered. The standard of care for subjects with solid tumors, such as rectal cancer patients, especially for Stage II and Stage III rectal cancer patients, is to treat the patient with a chemoradiation therapy regimen (e.g., 5-Fluorouracil (5-FU) or capecitabine+radiation) prior to surgical removal of the tumor. The neoadjuvant chemoradiation therapy regimen is intended to shrink the tumor to enhance the capacity to remove the tumor as well as to enhance the surgical outcome. Accordingly, the lack of detection of one or more of genomic instability, double stranded DNA breaks, enhanced gamma-H2AX foci, and/or and elevated levels of replication stress and/or DSB-signalling biomarkers in the patient's peripheral blood lymphocytes may significantly alter the standard of care in that the patient is not treated with pre-operative chemoradiation, thereby avoiding side effects of chemoradiation therapy where such is not likely to provide the patient with any substantial benefit. In some alternative embodiments, the standard of care may be altered such that the patient is administered a different chemotherapeutic agent instead of 5-Fluorouracil (5-FU) or capecitabine.

The detection or lack of detection of one or more of genomic instability, double stranded DNA breaks, enhanced gamma-H2AX foci, and/or and elevated levels of replication stress and/or DSB-signalling biomarkers may allow a patient to receive treatment counseling that can permit the patient to make more informed choices about a course of treatment. For example, the knowledge that the patient is unlikely to respond to a chemoradiation therapy regimen may permit the patient to agree to an alternative treatment regimen prior to surgery, or to opt for surgery without pre-operative chemoradiation therapy, or to opt for a different neoadjuvant chemotherapeutic regimen. In addition, in some embodiments, a patient may be identified and/or selected who will respond to chemoradiation. For such selected patients, the patients can be treated with chemoradiation.

The treatment methods may omit or adjust a chemotherapy-radiation therapy regimen where a lack of one or more of genomic instability, double stranded DNA breaks, elevated levels of gamma H2AX foci, and/or and elevated levels of replication stress and/or DSB-signalling biomarkers is detected in peripheral blood lymphocytes isolated from the patient.

In some embodiments, the subject, or human, may be "in need" of treatment, or "in need thereof" or suspected of being in need of the same. Such a subject will have been examined for the presence or absence of genomic instability, double stranded DNA breaks, elevated levels of gamma H2AX foci, and/or and elevated levels of replication stress and/or DSB-signalling biomarkers, such as described herein, and determined to be possessing genomic instability, double stranded DNA breaks, elevated levels of gamma H2AX foci, and/or and elevated levels of replication stress and/or DSB-signalling biomarkers. Such subjects, thus, will be in need of preoperative chemoradiation therapy prior to surgery to remove the tumor.

The present disclosure also provides methods for treating a subject having a solid tumor comprising: detecting the presence or absence of any one or more of i) genomic instability, ii) double stranded DNA breaks, iii) gamma-H2AX foci, and iv) a replication stress and/or DSB-signalling biomarker, in isolated peripheral blood lymphocytes from the subject having the solid tumor; and i) removing the solid tumor from the subject without preoperative chemoradiation therapy when the absence of an elevated level of all of i), ii), iii), and iv) compared to a subject not having a solid tumor exists; or ii) treating the subject with preoperative chemoradiation therapy prior to removing the solid tumor from the subject when the presence of an elevated level of any one or more of i), ii), iii), and iv) compared to a subject not having a solid tumor exists. In some embodiments, the methods of treatment (e.g., removing the solid tumor from the subject with and without preoperative chemoradiation therapy) are performed on subjects that have already been identified as having or not having any one or more of i) genomic instability, ii) double stranded DNA breaks, iii) gamma-H2AX foci, and iv) a replication stress and/or DSB-signalling biomarker, in isolated peripheral blood lymphocytes from the subject having the solid tumor (i.e., such subjects have been previously examined for such criteria).

In any of the embodiments described herein, the method can comprise detecting the presence or absence of any one or more of i) genomic instability, ii) double stranded DNA breaks, iii) gamma-H2AX foci, and iv) a replication stress and/or DSB-signalling biomarker, in isolated peripheral blood lymphocytes from the subject having the solid tumor. In any of the embodiments described herein, the method can comprise detecting the presence or absence of any two of i) genomic instability, ii) double stranded DNA breaks, iii) gamma-H2AX foci, and iv) a replication stress and/or DSB-signalling biomarker, in isolated peripheral blood lymphocytes from the subject having the solid tumor. In any of the embodiments described herein, the method can comprise detecting the presence or absence of any three of i) genomic instability, ii) double stranded DNA breaks, iii) gamma-H2AX foci, and iv) a replication stress and/or DSB-signalling biomarker, in isolated peripheral blood lymphocytes from the subject having the solid tumor. In any of the embodiments described herein, the method can comprise detecting the presence or absence of all four of i) genomic instability, ii) double stranded DNA breaks, iii) gamma-H2AX foci, and iv) a replication stress and/or DSB-signalling biomarker, in isolated peripheral blood lymphocytes from the subject having the solid tumor.

In any of the embodiments described herein, the subject can comprise the presence of any one or more of i) genomic instability, ii) double stranded DNA breaks, iii) gamma-H2AX foci, and iv) a replication stress and/or DSB-signalling biomarker, in isolated peripheral blood lymphocytes from the subject having the solid tumor. In any of the embodiments described herein, the subject can comprise the presence of any two of i) genomic instability, ii) double stranded DNA breaks, iii) gamma-H2AX foci, and iv) a replication stress and/or DSB-signalling biomarker, in isolated peripheral blood lymphocytes from the subject having the solid tumor. In any of the embodiments described herein, the subject can comprise the presence of any three of i) genomic instability, ii) double stranded DNA breaks, iii) gamma-H2AX foci, and iv) a replication stress and/or DSB-signalling biomarker, in isolated peripheral blood lymphocytes from the subject having the solid tumor. In any of the embodiments described herein, the subject can comprise the presence of all four of i) genomic instability, ii) double stranded DNA breaks, iii) gamma-H2AX foci, and iv) a replication stress and/or DSB-signalling biomarker, in isolated peripheral blood lymphocytes from the subject having the solid tumor.

The following representative embodiments are presented:

Embodiment 1. A method for treating rectal cancer in a human comprising: a) detecting the presence or absence of genomic instability, double stranded DNA breaks, and/or levels of gamma-H2AX foci that are elevated over desired levels of gamma-H2AX foci in the peripheral blood lymphocytes from a human having a Stage II or Stage III rectal tumor; and b) where the presence of genomic instability, double stranded DNA breaks, and/or elevated levels of gamma-H2AX foci are detected, treating the human with preoperative chemoradiation therapy prior to surgery to remove the tumor; or where the absence of genomic instability, double stranded DNA breaks, and/or elevated levels of gamma-H2AX foci are detected, removing the tumor by surgery without preoperative chemoradiation therapy.

Embodiment 2. The method according to embodiment 1, wherein the human has a Stage II rectal tumor.

Embodiment 3. The method according to embodiment 1, wherein the human has a Stage III rectal tumor.

Embodiment 4. A method for treating rectal cancer in a human comprising: a) detecting the presence or absence of double stranded DNA breaks in the peripheral blood lymphocytes from a human having a Stage II or Stage III rectal tumor; and b) where the presence of double stranded DNA breaks is detected, treating the human with preoperative chemoradiation therapy prior to surgery to remove the tumor; or where the absence of double stranded DNA breaks is detected, removing the tumor by surgery without preoperative chemoradiation therapy.

Embodiment 5. The method according to embodiment 4, wherein the human has a Stage II rectal tumor.

Embodiment 6. The method according to embodiment 4, wherein the human has a Stage III rectal tumor.

Embodiment 7. A method for treating rectal cancer in a human comprising: a) detecting the presence or absence of double stranded DNA breaks and gamma-H2AX foci that are elevated over desired levels of gamma-H2AX foci in the peripheral blood lymphocytes from a human having a Stage II or Stage III rectal tumor; and b) where the presence of double stranded DNA breaks and elevated levels of gamma-H2AX foci are detected, treating the human with preoperative chemoradiation therapy prior to surgery to remove the tumor; or where the absence of double stranded DNA breaks and/or elevated levels of gamma-H2AX foci are detected, removing the tumor by surgery without preoperative chemoradiation therapy.

Embodiment 8. The method according to embodiment 7, wherein the human has a Stage II rectal tumor.

Embodiment 9. The method according to embodiment 7, wherein the human has a Stage III rectal tumor.

Embodiment 10. A method for treating rectal cancer in a human comprising: a) detecting the presence or absence of genomic instability in the peripheral blood lymphocytes from a human having a Stage II or Stage III rectal tumor; and b) where the presence of genomic instability is detected, treating the human with preoperative chemoradiation therapy prior to surgery to remove the tumor; or where the absence of genomic instability is detected, removing the tumor by surgery without preoperative chemoradiation therapy.

Embodiment 11. The method according to embodiment 10, wherein the human has a Stage II rectal tumor.

Embodiment 12. The method according to embodiment 10, wherein the human has a Stage III rectal tumor.

Embodiment 13. A method for treating rectal cancer in a human comprising: a) detecting the presence or absence of genomic instability and double stranded DNA breaks in the peripheral blood lymphocytes from a human having a Stage II or Stage III rectal tumor; and b) where the presence of genomic instability and double stranded DNA breaks are detected, treating the human with preoperative chemoradiation therapy prior to surgery to remove the tumor; or where the absence of genomic instability and double stranded DNA breaks are detected, removing the tumor by surgery without preoperative chemoradiation therapy.

Embodiment 14. The method according to embodiment 13, wherein the human has a Stage II rectal tumor.

Embodiment 15. The method according to embodiment 13, wherein the human has a Stage III rectal tumor.

Embodiment 16. A method for treating rectal cancer in a human comprising: a) detecting the presence or absence of genomic instability and levels of gamma-H2AX foci that are elevated over desired levels of gamma-H2AX foci in the peripheral blood lymphocytes from a human having a Stage II or Stage III rectal tumor; and b) where the presence of genomic instability and elevated levels of gamma-H2AX foci are detected, treating the human with preoperative chemoradiation therapy prior to surgery to remove the tumor; or where the absence of genomic instability and elevated levels of gamma-H2AX foci are detected, removing the tumor by surgery without preoperative chemoradiation therapy.

Embodiment 17. The method according to embodiment 16, wherein the human has a Stage II rectal tumor.

Embodiment 18. The method according to embodiment 16, wherein the human has a Stage III rectal tumor.

Embodiment 19. A method for treating rectal cancer in a human comprising: a) detecting the presence or absence of double stranded DNA breaks and levels of gamma-H2AX foci that are elevated over desired levels of gamma-H2AX foci in the peripheral blood lymphocytes from a human having a Stage II or Stage III rectal tumor; and b) where the presence of double stranded DNA breaks and elevated levels of gamma-H2AX foci are detected, treating the human with preoperative chemoradiation therapy prior to surgery to remove the tumor; or where the absence of double stranded DNA breaks, and elevated levels of gamma-H2AX foci are detected, removing the tumor by surgery without preoperative chemoradiation therapy.

Embodiment 20. The method according to embodiment 19, wherein the human has a Stage II rectal tumor.

Embodiment 21. The method according to embodiment 19, wherein the human has a Stage III rectal tumor.

Embodiment 22. A method for diagnosing a subject as a candidate for removal of a solid tumor without preoperative chemoradiation therapy comprising: detecting the presence or absence of any one or more of i) genomic instability, ii) double stranded DNA breaks, iii) gamma-H2AX foci, and iv) a replication stress and/or DSB-signalling biomarker, in isolated peripheral blood lymphocytes from the subject having the solid tumor; wherein the absence of an elevated level of all of i), ii), iii), and iv) compared to a subject not having a solid tumor indicates that the subject is a candidate for removal of the solid tumor without preoperative chemoradiation therapy; and wherein the presence of an elevated level of any one or more of i), ii), iii), and iv) compared to a subject not having a solid tumor indicates that the subject is a candidate for removal of the solid tumor after receiving preoperative chemoradiation therapy.

Embodiment 23. The method according to embodiment 22, wherein the presence or absence of at least any two of i) genomic instability, ii) double stranded DNA breaks, iii) gamma-H2AX foci, and iv) a replication stress and/or DSB-signalling biomarker, are detected in isolated peripheral blood lymphocytes from the subject having the solid tumor.

Embodiment 24. The method according to embodiment 22, wherein the presence or absence of at least any three of i) genomic instability, ii) double stranded DNA breaks, iii) gamma-H2AX foci, and iv) a replication stress and/or DSB-signalling biomarker, are detected in isolated peripheral blood lymphocytes from the subject having the solid tumor.

Embodiment 25. The method according to embodiment 22, wherein the presence or absence of i) genomic instability, ii) double stranded DNA breaks, iii) gamma-H2AX foci, and iv) a replication stress and/or DSB-signalling biomarker, are detected in isolated peripheral blood lymphocytes from the subject having the solid tumor.

Embodiment 26. The method according to any one of embodiments 22 to 25, wherein the solid tumor is rectal cancer, esophageal cancer, or lung cancer.

Embodiment 27. The method according to embodiment 26, wherein the rectal cancer is Stage II rectal cancer or Stage III rectal cancer.

Embodiment 28. The method according to any one of embodiments 22 to 27, wherein the replication stress biomarker is replication protein A (RPA), ataxia telangiectasia and Rad3-related (ATR), or checkpoint kinase 1 (CHK1).

Embodiment 29. The method according to any one of embodiments 22 to 28, wherein the DSB-signalling biomarker is phospho-ataxia telangiectasia mutated (phospho-ATM) or checkpoint kinase 2 (CHK2).

Embodiment 30. A method for treating a subject having a solid tumor comprising: detecting the presence or absence of any one or more of i) genomic instability, ii) double stranded DNA breaks, iii) gamma-H2AX foci, and iv) a replication stress and/or DSB-signalling biomarker, in isolated peripheral blood lymphocytes from the subject having the solid tumor; and i) removing the solid tumor from the subject without preoperative chemoradiation therapy when the absence of an elevated level of all of i), ii), iii), and iv) compared to a subject not having a solid tumor exists; or ii) treating the subject with preoperative chemoradiation therapy prior to removing the solid tumor from the subject when the presence of an elevated level of any one or more of i), ii), iii), and iv) compared to a subject not having a solid tumor exists.

Embodiment 31. The method according to embodiment 30, wherein the presence or absence of at least any two of i) genomic instability, ii) double stranded DNA breaks, iii) gamma-H2AX foci, and iv) a replication stress and/or DSB-signalling biomarker, are detected in isolated peripheral blood lymphocytes from the subject having the solid tumor.

Embodiment 32. The method according to embodiment 30, wherein the presence or absence of at least any three of i) genomic instability, ii) double stranded DNA breaks, iii) gamma-H2AX foci, and iv) a replication stress and/or DSB-signalling biomarker, are detected in isolated peripheral blood lymphocytes from the subject having the solid tumor.

Embodiment 33. The method according to embodiment 30, wherein the presence or absence of i) genomic instability, ii) double stranded DNA breaks, iii) gamma-H2AX foci, and iv) a replication stress and/or DSB-signalling biomarker, are detected in isolated peripheral blood lymphocytes from the subject having the solid tumor.

Embodiment 34. The method according to any one of embodiments 30 to 33, wherein the solid tumor is rectal cancer, esophageal cancer, or lung cancer.

Embodiment 35. The method according to embodiment 34, wherein the rectal cancer is Stage II rectal cancer or Stage III rectal cancer.

Embodiment 36. The method according to any one of embodiments 30 to 35, wherein the replication stress biomarker is replication protein A (RPA), ataxia telangiectasia and Rad3-related (ATR), or checkpoint kinase 1 (CHK1).

Embodiment 37. The method according to any one of embodiments 30 to 36, wherein the DSB-signalling biomarker is phospho-ataxia telangiectasia mutated (phospho-ATM) or checkpoint kinase 2 (CHK2).

The following examples are provided to describe the embodiments set forth herein in greater detail. They are intended to illustrate, not to limit, the embodiments set forth herein.

EXAMPLES

Example 1

Genomic Instability as a Biomarker for CRT Responsiveness

In this study, genomic instability was evaluated as a biomarker of CRT response in locally advanced rectal cancer. These studies extend previous approaches in familial colorectal cancers (FCRC). Briefly, in the previous studies it was shown that a mild to moderate form of constitutional genomic instability is common in genetically undefined Familial Colorectal Cancer (uFCRC).

Constitutional genomic instability can be detected by assays of patient peripheral blood lymphocytes. Using such PBL cultures, elevated levels of gamma-H2AX, a marker of DNA double strand breaks (DSB), were observed from 18/25 high-risk colon cancer patients vs. 1/25 normal controls (AUC=0.85, P=0.001). In this assay, patient and matched control PBLs were immunostained using an antibody against phosphorylated gamma-H2AX. The conditions tested are at baseline or post treatment with DNA damaging agents like aphidicolin and UV light to induce DNA double strand breaks (DSBs). In the presence of DNA DSBs, H2AX gets phosphorylated to gamma-H2AX and forms nuclear foci, which can be quantified manually or in an automated fashion. Using this method, it was shown that cases can be separated from matched controls with high sensitivity and specificity (AUC=0.85). Whole exome sequencing was also performed in these cases, and this identified candidate disease-causing gene variants that lie in DNA DSB repair pathways not previously linked to FCRC. Each variant was absent or rare in single nucleotide polymorphism (SNP) databases, alters a highly conserved amino acid, and is predicted to be damaging by multiple functional predictor programs (SIFT, PolyPhen2, PROVEAN, MutationAssessor). Further, knockdown of variant genes in CRC cell line (HCT116) showed increased DSBs with or without treatment with DNA damaging agents. Increased gamma-H2AX levels were also documented in two independent EBV-transformed B-cell lines derived from a patient compared to two independent lines from an age- and sex-matched control, corroborating evidence for a DNA double strand break defect in this patient and suggesting the utility of such lines for study of this defect. Evidence of gene variants in DNA DSB repair pathways was also documented in polyposis patients.

In this study with rectal cancer, it was rationalized that patients predisposed to rectal cancer development also exhibit genomic instability, double stranded DNA breaks (DSBs), and/or enhanced gamma-H2AX foci. Thus, this combination of genomic instability, double stranded DNA breaks, and/or enhanced gamma-H2AX foci may serve as a biomarker for response to DNA damaging CRT in rectal cancer.

Here, patient PBLs (from biosample repository consented patients) were utilized to assess cellular phenotypes. The rectal cancer patients were divided into a pilot group of responders and non-responders based on their NeoAdjuvant Rectal (NAR) score. The NAR score was calculated based on data supported by the Valentini nomogram for Overall Survival (OS), but only using the clinical T stage and pathologic T and N stages. In another study, the patient cohort was divided into responders (n=16) and non-responders (n=13) using the NAR score scheme. At the time of testing, patient PBLs were cultured and either treated with vehicle (baseline levels) or treated with different DNA damaging agents aphidicolin or ionizing radiation, to induce DNA double strand breaks (DSBs). PBLs were then immunostained using an antibody against phosphorylated gamma-H2AX. In the presence of DNA DSBs, H2AX will be phosphorylated to gamma-H2AX and form nuclear foci, which can be quantified manually or in an automated fashion.

Through these studies, even at baseline the data indicate significant segregation of responder and non-responders groups (p<0.023) (see, FIG. 1). After controlling for any characteristics such as age, sex and time from chemotherapy, the data are again statistically significant between the two groups (p<0.028). These data show statistically significant segregation of the two groups when DNA damaging treatments, aphidicolin and ionizing radiation (p<0.05), are utilized.

Referring specifically to FIG. 1, primary T-cells from CRT responder (n=16) and CRT non-responder (n=13) rectal cancer patients were stimulated by PHA and IL-2, then treated with vehicle (baseline), aphidicolin or ionizing radiation, and stained for nuclear gamma-H2AX foci. Percent gamma-H2AX foci in vehicle or baseline treated patients (p=0.028, significant), aphidicolin (p=0.038, significant) and ionizing radiation or irradiation (p=0.0314, significant). The data were statistically adjusted for age, sex and time from treatment.

Thus, a novel test for assessing CRT response for rectal cancer in patient blood cells has been developed. The test utilizes increased gamma H2AX or DNA double strand breaks as a biomarker for ongoing genomic instability. Including low doses of DNA damaging agents further brings out the defective DNA damage response.

Example 2

Markers of DNA-Damage Response and Repair Signaling

Figure 2:
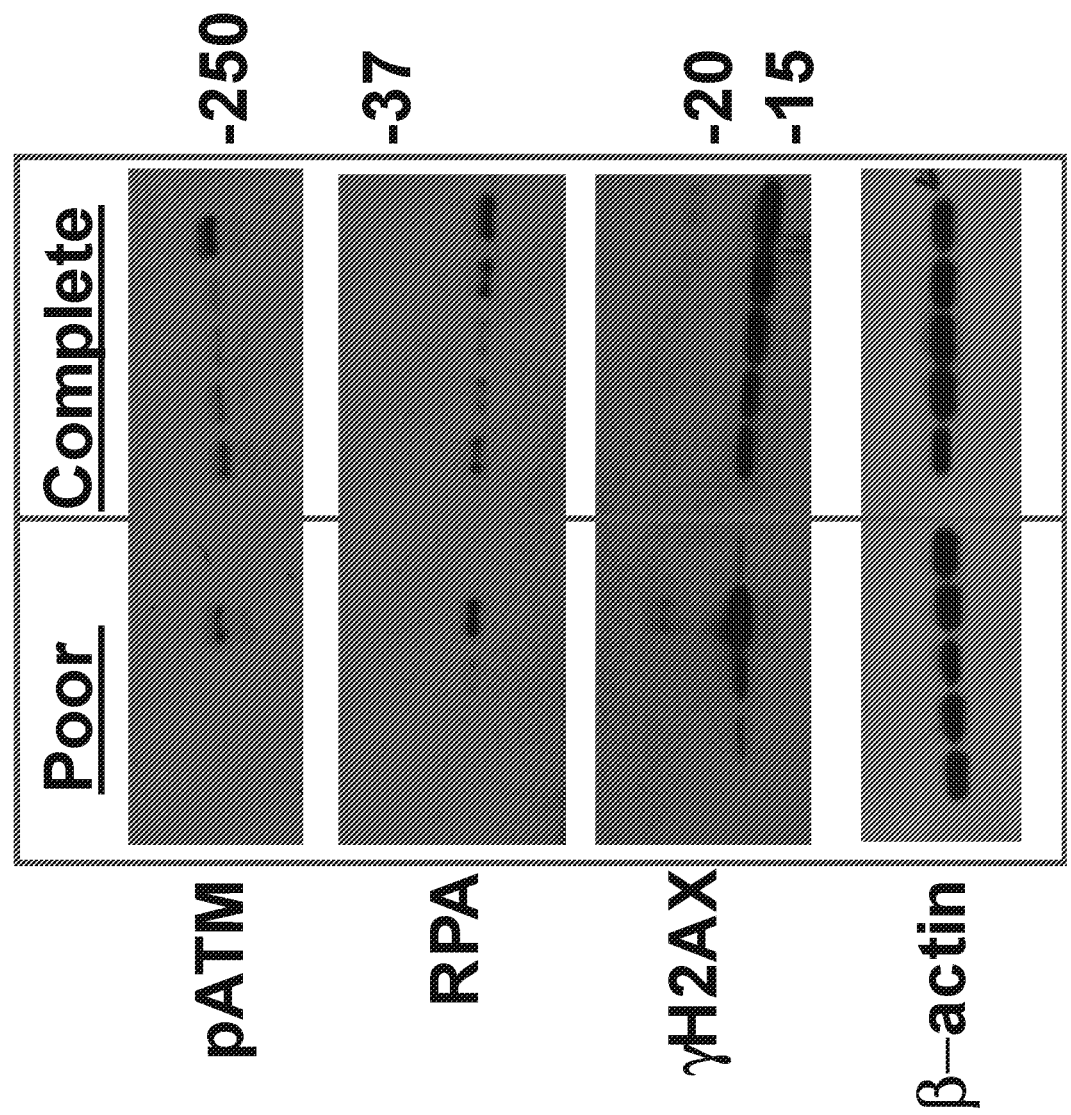
FIG. 2 shows the expression of DNA-damage response and repair proteins is elevated in pPBLs of complete responders compared to poor responders (rectal cancer patients treated with nCRT).

Additional markers of DNA-damage response and repair signaling were examined for their correlation with the γH2AX findings. Whole-cell lysates were prepared from primary PBLs of patients who either had a complete response or poor response to nCRT. Briefly, PBLs were pelleted, cell lysates were prepared, and Western blot analysis was performed for the respective proteins (see, FIGS. 2) and β-actin was used as a loading control. Total protein levels were quantified and normalized to the loading control. Primary antibodies were used from standard suppliers. As shown in FIG. 2, markers of replication stress (e.g., RPA) and DSB-signaling (e.g., phospho-ATM) were also up-regulated in pPBLs from complete responders compared to poor responders (n=5 of each). The Western blot shows representative images of DNA-DRR markers phospho-ATM, RPA and γH2AX; β-actin, loading control. Lanes indicate individual patients. Numbers indicate protein size. These results indicate that at least in the patients that have been examined, additional markers correlate with treatment response.

The present disclosure is not limited to the embodiments described and exemplified above, but is capable of variation and modification within the scope of the appended claims. Various publications, including patents, published applications, accession numbers, technical articles and scholarly articles are cited throughout the specification. Each of these cited publications is incorporated by reference, in its entirety and for all purposes, in this document.

What is claimed is:

1. A method for treating a subject having a solid tumor comprising:
   detecting the presence or absence of any one or more of
   i) genomic instability, ii) double stranded deoxyribonucleic acid (DNA) breaks, iii) gamma-H2A hi stone family member X (gamma-H2AX) foci, and iv) a replication stress and/or double stranded break-signalling (DSB-signalling) biomarker, in isolated peripheral blood lymphocytes from the subject having the solid tumor; and
   i) removing the solid tumor from the subject without preoperative chemoradiation therapy when there is an absence of an elevated level of all of i), ii), iii), and iv) compared to a subject not having a solid tumor exists; or
   ii) treating the subject with preoperative chemoradiation therapy prior to removing the solid tumor from the subject when an elevated level of any one or more of i), ii), iii), and iv) is present compared to a subject not having a solid tumor exists.

2. The method according to claim 1, wherein the presence or absence of at least any two of i) genomic instability, ii) double stranded DNA breaks, iii) gamma-H2AX foci, and iv) a replication stress and/or DSB-signalling biomarker, are detected in isolated peripheral blood lymphocytes from the subject having the solid tumor.

3. The method according to claim 1, wherein the presence or absence of at least any three of i) genomic instability, ii) double stranded DNA breaks, iii) gamma-H2AX foci, and iv) a replication stress and/or DSB-signalling biomarker, are detected in isolated peripheral blood lymphocytes from the subject having the solid tumor.

4. The method according to claim 1, wherein the presence or absence of i) genomic instability, ii) double stranded DNA breaks, iii) gamma-H2AX foci, and iv) a replication stress and/or DSB-signalling biomarker, are detected in isolated peripheral blood lymphocytes from the subject having the solid tumor.

5. The method according to claim 1, wherein the solid tumor is rectal cancer, esophageal cancer, or lung cancer.

6. The method according to claim 5, wherein the rectal cancer is Stage II rectal cancer or Stage III rectal cancer.

7. The method according to claim 1, wherein the replication stress biomarker is replication protein A (RPA), ataxia telangiectasia and Rad3-related (ATR), or checkpoint kinase 1 (CHK1).

8. The method according to claim 1, wherein the DSB-signalling biomarker is phospho-ataxia telangiectasia mutated (phospho-ATM) or checkpoint kinase 2 (CHK2).

9. The method according to claim 1, wherein the solid tumor is rectal cancer.

10. The method according to claim 1, wherein the solid tumor is esophageal cancer.

11. The method according to claim 1, wherein the solid tumor is lung cancer.

* * * * *